(12) United States Patent
Banfi et al.

(10) Patent No.: US 8,519,160 B2
(45) Date of Patent: Aug. 27, 2013

(54) PROCESS FOR THE PREPARATION OF ROTIGOTINE

(75) Inventors: Aldo Banfi, Rodano (IT); Gialunca Belogi, Rodano (IT); Claudio Fuganti, Rodano (IT); Roberta Pizzocaro, Rodano (IT)

(73) Assignee: Fidia Farmaceutici S.p.A., Abano Terme (IT)

( * ) Notice: Subject to any disclaimer, the term of this patent is extended or adjusted under 35 U.S.C. 154(b) by 162 days.

(21) Appl. No.: 13/120,682

(22) PCT Filed: Sep. 24, 2009

(86) PCT No.: PCT/IB2009/006934
§ 371 (c)(1),
(2), (4) Date: Jun. 13, 2011

(87) PCT Pub. No.: WO2010/035111
PCT Pub. Date: Apr. 1, 2010

(65) Prior Publication Data
US 2011/0230541 A1 Sep. 22, 2011

(30) Foreign Application Priority Data
Sep. 26, 2008 (IT) .................. MI2008A1713

(51) Int. Cl.
*C07D 333/20* (2006.01)
(52) U.S. Cl.
USPC .............................................. 549/75
(58) Field of Classification Search
USPC .............................................. 549/75
See application file for complete search history.

(56) References Cited

U.S. PATENT DOCUMENTS

| 4,564,628 A | 1/1986 | Horn |
| 5,382,596 A | 1/1995 | Sleevi et al. |

FOREIGN PATENT DOCUMENTS

| EP | 0 325 964 | 8/1989 |
| WO | 01/38321 | 5/2001 |

OTHER PUBLICATIONS

Sonesson et al., "Synthesis and Evaluation of Pharmacological and Pharmacokinetic Properties of Monopropyl Analogs of 5-, 7-, and 8-[[(Trifluoromethyl)sulfonyl]oxy]-2-aminotetralins: Central Dopamine and Serotonin Receptor Activity" J. of Medicinal Chemistry, vol. 38, No. 8, Jan. 1, 1995, pp. 1319-1329.

*Primary Examiner* — Taofiq A Solola
(74) *Attorney, Agent, or Firm* — Lucas & Mercanti, LLP

(57) ABSTRACT

A process for the preparation of Rotigotine (I) and of pharmaceutically acceptable salts thereof, which comprises the reductive amination of an amine of formula 6 with the 2-thienylacetic acid-sodium boron hydride complex and which makes use of hydrobromide 5 as an intermediate (II). The process is advantageous from the industrial point of view in that it allows to obtain Rotigotine with high enantiomeric purity starting from optically active 5,6,7,8-tetrahydro-6-(S)-N-propylamino-1-methoxynaphthalene (2), avoiding the use of dangerous reactives, the need for difficult chromatographic separation or the formation of by-products. Furthermore, two novel crystalline forms are disclosed.

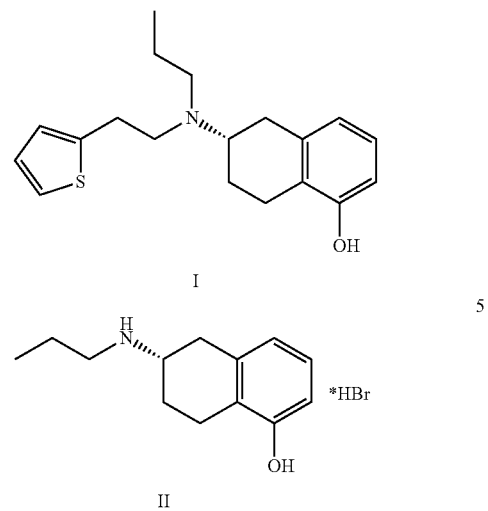

3 Claims, 6 Drawing Sheets

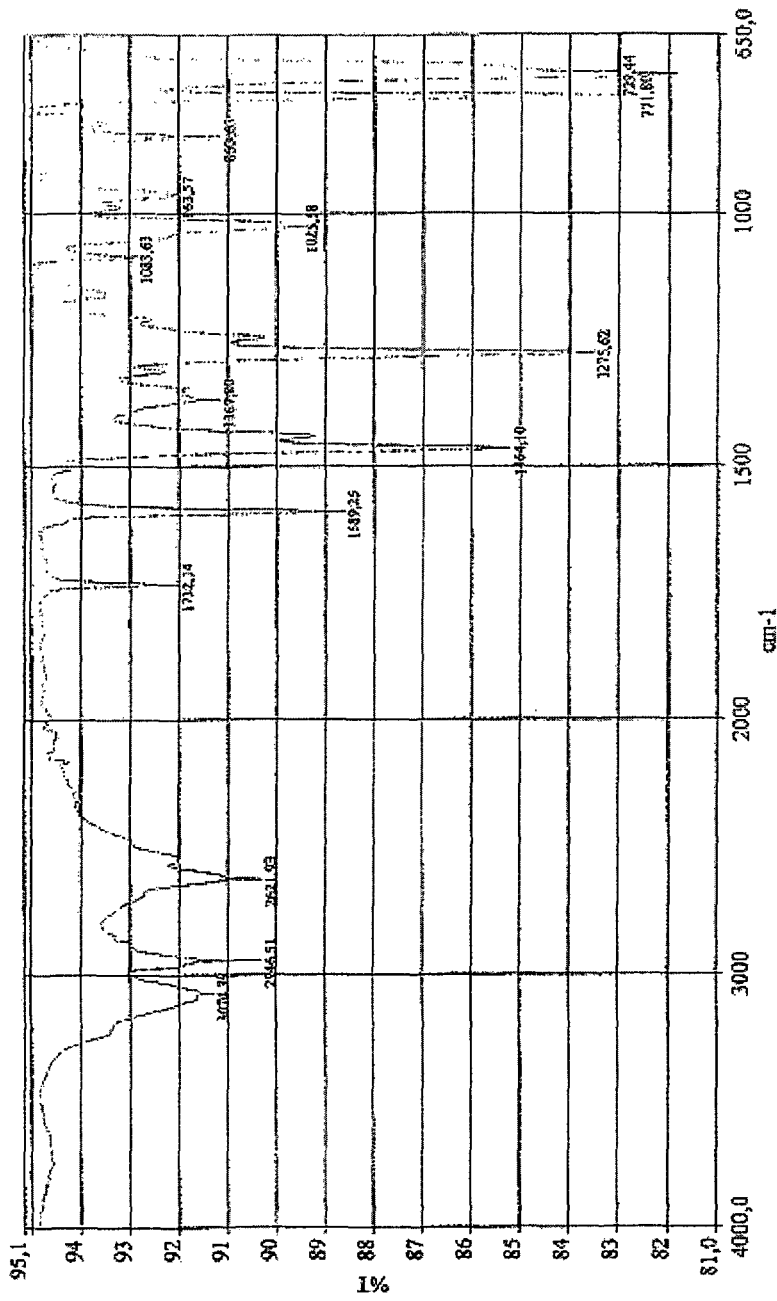
Figure 1: IR spectrum of Rotigotine hydrochloride Form A

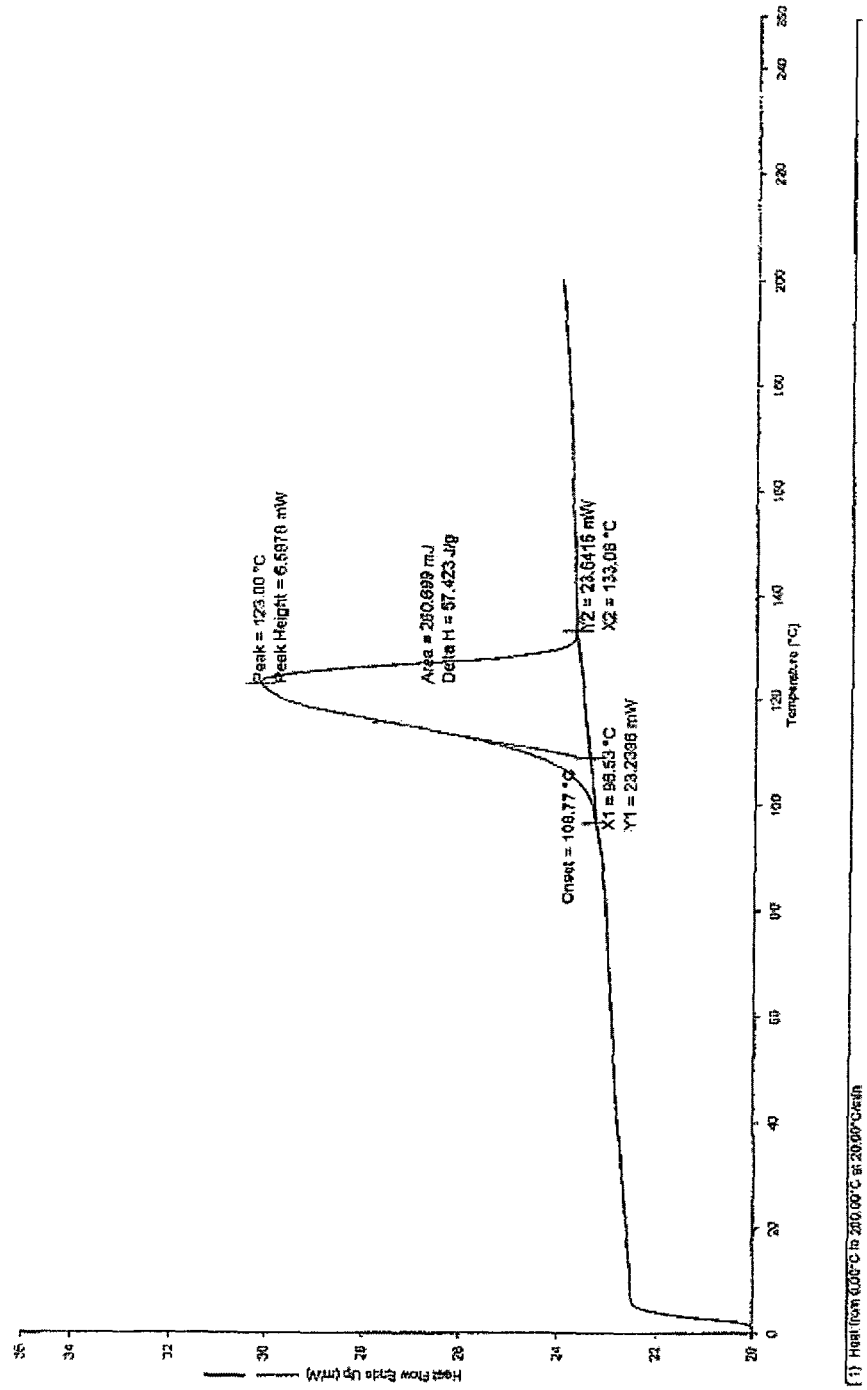
Figure 2: DSC of Rotigotine hydrochloride Form A

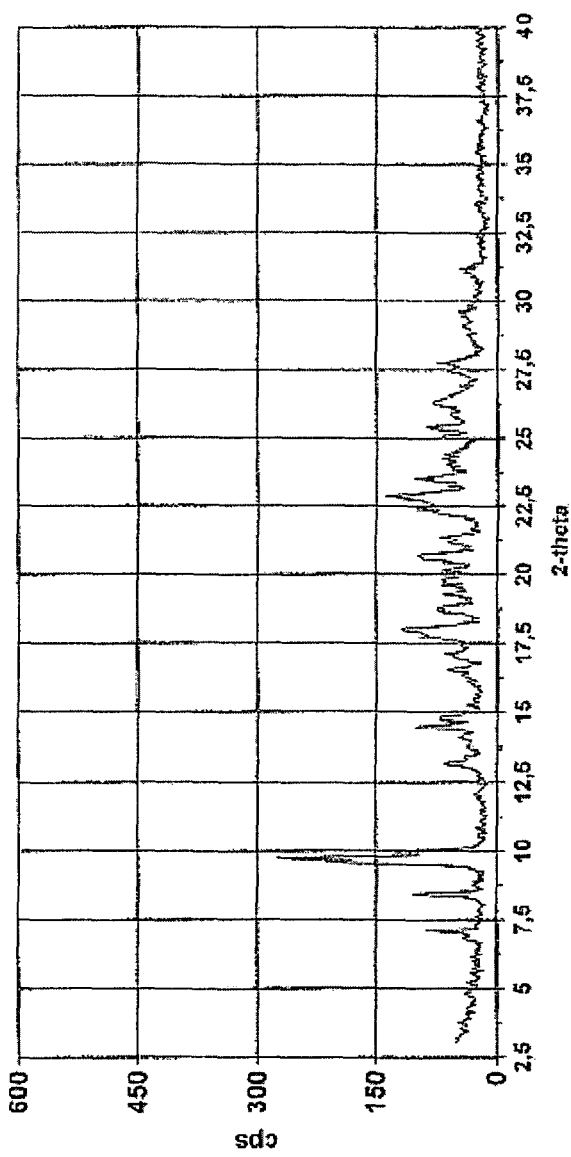
Figure 3: X-ray spectrum of Rotigotine hydrochloride Form A

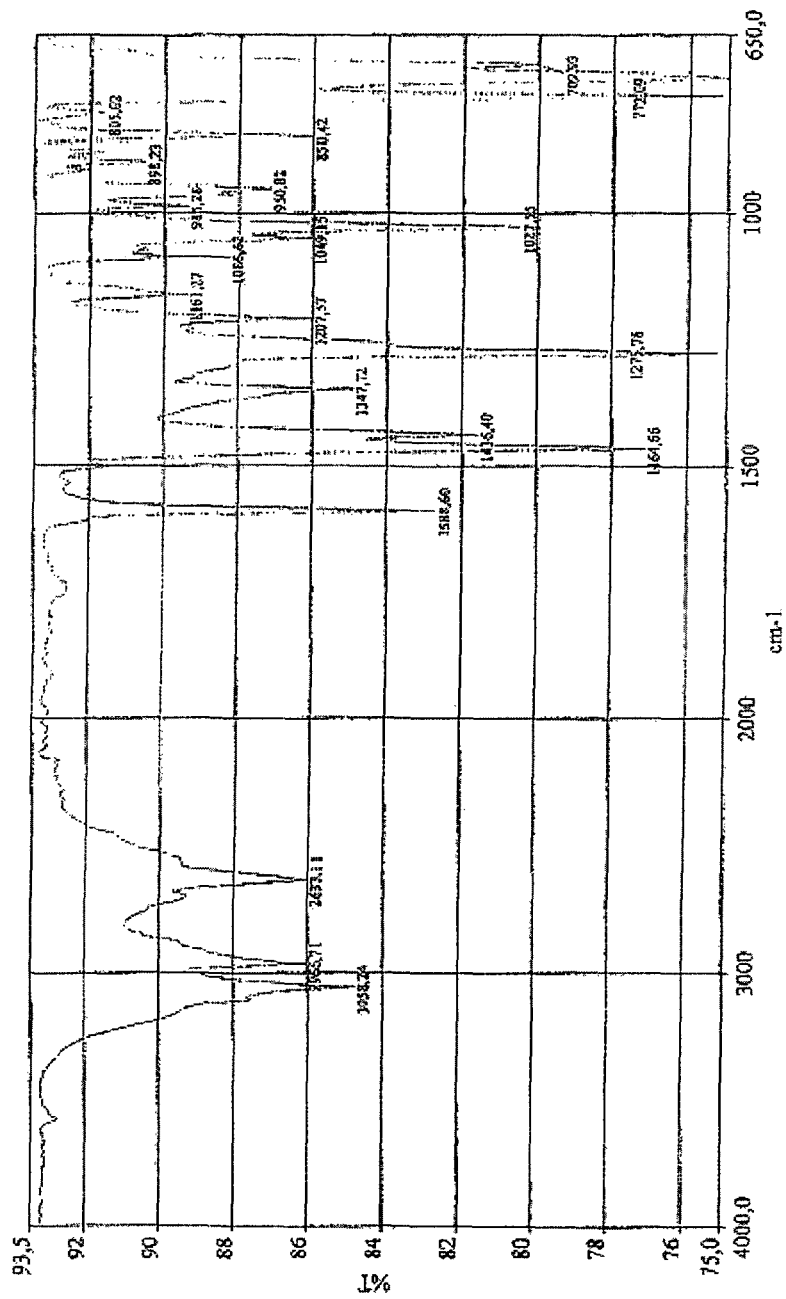
Figure 4: IR spectrum of Rotigotine hydrochloride Form B

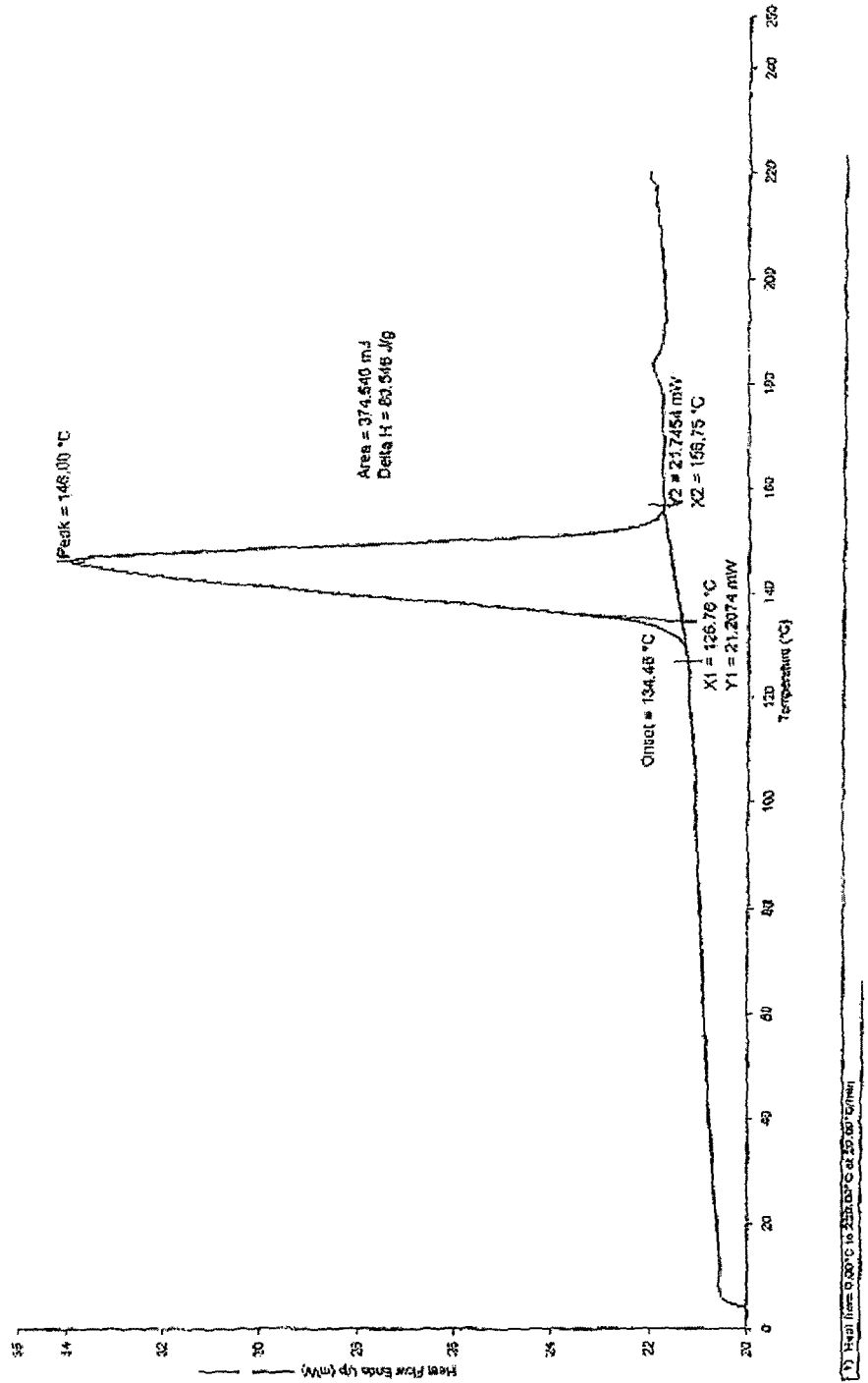
Figure 5: DSC of Rotigotine hydrochloride Form B

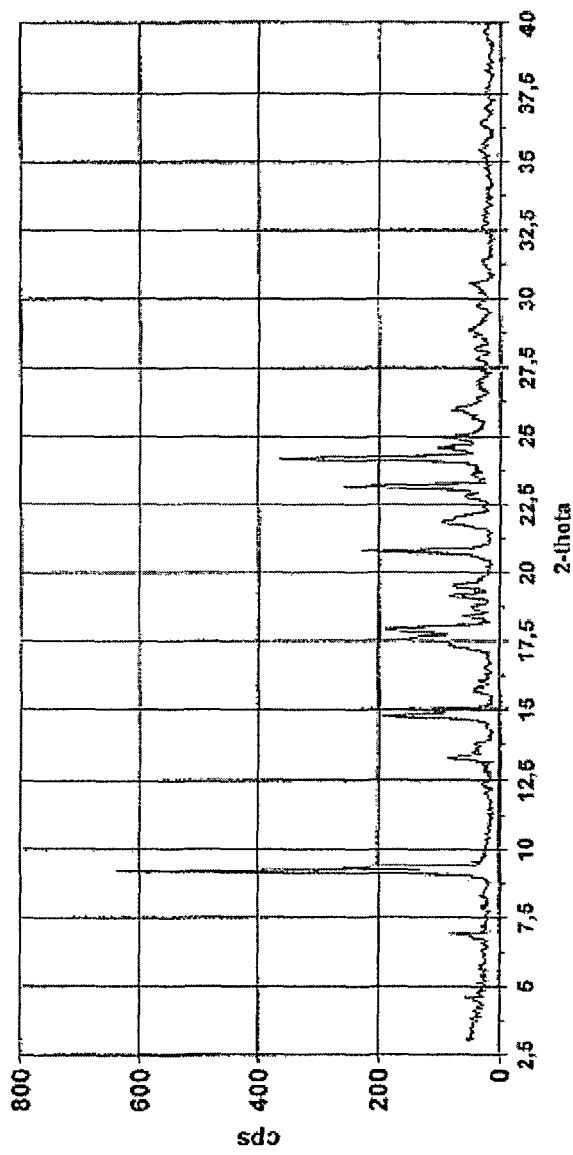
Figure 6: X-ray spectrum of Rotigotine hydrochloride Form B

PROCESS FOR THE PREPARATION OF ROTIGOTINE

This application is a U.S. national stage of PCT/IB2009/006934 filed on Sep. 24, 2009 which claims priority to and the benefit of Italian Application No. MI2008A1713 filed on Sep. 26, 2008, the contents of which are incorporated herein by reference.

FIELD OF THE INVENTION

The present invention relates to 5,6,7,8-tetrahydro-6-S-[N-propyl-2-(2-thienyl)-N-ethyl]-amino-1-naphthalenol, commonly known as Rotigotine (1), a medicament used in the therapy of the early stages of idiopathic Parkinson's disease, usually in the form of its hydrochloride salt.

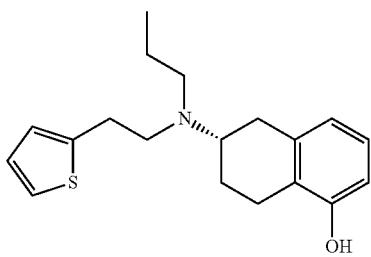

BACKGROUND OF THE INVENTION

The preparation and therapeutical uses of Rotigotine were first disclosed in U.S. Pat. No. 4,564,628 and U.S. Pat. No. 4,885,308. The product currently pharmaceutically used is the S enantiomeric form or its hydrochloride salt, the known syntheses of which involve 2-N-propyl-5-methoxy tetraline S enantiomer (2) as the key intermediate

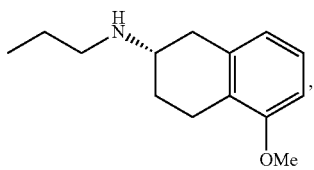

which is prepared by optical resolution of the racemate according to what described in U.S. Pat. No. 4,968,837.

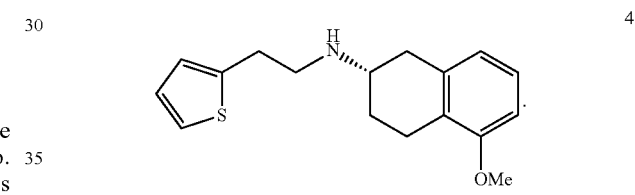

A number of procedures for the transformation of amine 2 into Rotigotine are disclosed. Among them, a procedure involves heating 2 in xylene with 2-thienylacetic acid and the trimethylamine-borane complex (U.S. Pat. No. 4,564,628 and *Pharmaceutisch Weekblad Sci. Ed.* 1985, 7, 208-211), which affords 5,6,7,8-tetrahydro-6-S-[N-propyl-2-(2-thienyl)-N-ethyl]-amino-1-methoxynaphthalene 3.

The trimethylamine-borane complex is an expensive, flammable product; therefore, this method for linking the thienylacetic chain to the secondary nitrogen of 2 is industrially problematic, due to the known instability of boron hydrides at high temperatures.

Transformation of 3 into Rotigotine, which is reported in the patents cited above and consists in hydrolyzing the methyl ether to free the phenol group, is carried out by treatment with boron tribromide at low temperature (−30° C. to −45° C.) in inert solvents. After completion of the reaction, the boron tribromide excess should be destroyed by addition of methanol, thereby forming trimethyl borate. This treatment is expensive, technically cumbersome and gives rise to polluting by-products. When using 48% hydrobromic acid under reflux for the conversion of 3 into Rotigotine, which is an established procedure for hydrolyzing phenol ethers, Rotigotine is formed together with a considerable amount of 5,6,7,8-tetrahydro-6-S-[N-(2-thienyl)-ethyl]amino-1-methoxynaphthalene 4, namely the de-alkylation product of the amino nitrogen

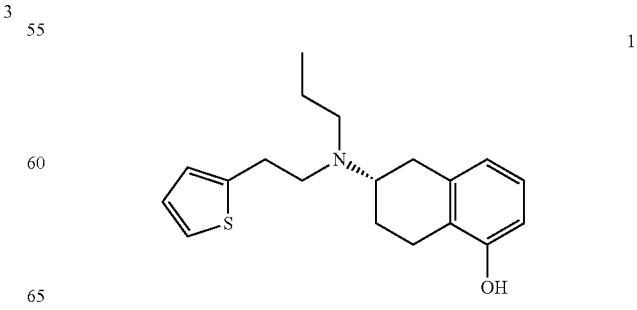

The structural similarity of 4 and Rotigotine makes the separation thereof through physical methods (crystallization and/or chromatography) exceedingly problematic.

It would therefore be useful to provide a process for the preparation of Rotigotine starting from the resolved amine 2 which is industrially more advantageous.

DISCLOSURE OF THE INVENTION

Object of the present invention is a process for the preparation of Rotigotine 1 or a pharmaceutically acceptable salt thereof, comprising the following steps:

a) demethylation of 5,6,7,8-tetrahydro-6-(S)-N-propylamino-1-methoxynaphthalene 2

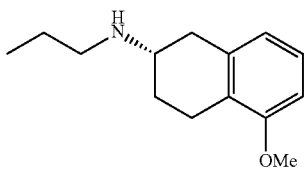

by refluxing in 48% HBr, to afford 2-N-propyl-5-hydroxy tetraline hydrobromide 5

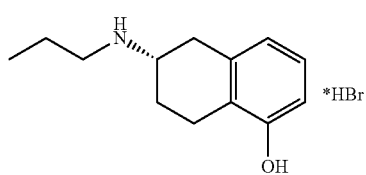

b) liberation of 2-N-propyl-5-hydroxy tetraline base 6

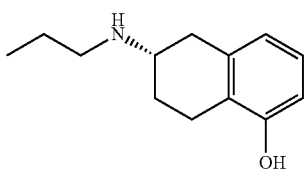

c) reductive amination reaction between amine 6 and 2-thienylacetic acid-sodium boron hydride complex in aprotic solvents selected from e.g. hydrocarbons, such as toluene, chlorinated solvents, such as methylene chloride or chloroform, esters, such as ethyl or butyl acetate and ethers, such as isopropyl and isobutyl ether, at temperatures ranging from 80 to 90° C., to afford Rotigotine 1;

d) optional salification of Rotigotine 1 with a pharmaceutically acceptable acid, preferably hydrochloric acid.

Therefore, the process of the invention differs from those of the prior art that:

a. it proceeds through the phenol amine 6 and b. the 2-thienylethyl chain is inserted at the nitrogen of 6 by reductive amination, using the 2-thienylacetic acid-sodium boron hydride complex in toluene.

According to a particular embodiment of the invention, an amine 2 with enantiomeric excess (ee) even lower than 0.94 is used as the starting product and the hydrobromide 5 is subsequently recrystallized to increase the enantiomeric purity.

In fact, de-O-methylation of 2 to give 5 takes place in high yields and it has been observed that, when using an amine 2 with enantiomeric excess (ee) of 0.94, the hydrobromide 5 obtained by precipitation at the end of the process has ee 0.98. Therefore, precipitation from the hydrobromic acid aqueous solution already involves after completion of the demethylation reaction such an increase in enantiomeric purity as to provide enantiomerically pure Rotigotine at the end of the synthesis process.

The hydrobromide salt 5 is therefore particularly advantageous and is a further aspect of the invention.

The introduction of the 2-thienylethyl chain at the secondary nitrogen of 6 using the preformed complex between sodium borohydride and 2-thienylacetic acid in toluene as the reagent is advantageous on an industrial scale, as sodium borohydride is much less expensive than the trimethylamine-borane complex; furthermore, the latter reagent requires the use of xylene under reflux, whereas toluene at 80-90° C. is sufficient when using sodium borohydride.

It has also been found that crystallization of Rotigotine hydrochloride from a mixture consisting of ethanol and ethyl acetate provides a crystalline form herein referred to as Form A, whereas crystallization of Rotigotine hydrochloride Form A from a mixture consisting of ethanol and hexane provides a crystalline form herein referred to as Form B, whose respective chemical-physical characterizations are reported in FIGS. 1-6 (DRX diffractograms, IR spectra and DSC scanning). In particular, Form A can be obtained taking up Rotigotine hydrochloride obtained by salification of Rotigotine with hydrochloric acid in about 10 ml of ethanol per gram of hydrochloride and heating under reflux; an equal volume of ethyl acetate is then added and the mixture is left cooling until crystallization. Form A is characterized by following infrared, DSC and X-ray spectra:

IR ($cm^{-1}$): 3074; 2946; 2621; 1732; 1589; 1464; 1367; 1275; 1083; 1025; 963; 850; 771; 729.

DSC: onset temperature: 108.8° C.; peak temperature: 123.0° C.

X-ray spectrum (2θ): 7.1; 8.4; 9.8; 10.0; 13.2; 14.5; 14.8; 17.1; 17.8; 18.0; 18.8; 20.7; 22.9; 23.5; 25.4.

Form B can be obtained taking up Form A in ethanol (approximately 10 ml of ethanol per gram of Form A), heating under reflux and adding an equal volume of hexane; Rotigotine hydrochloride Form B precipitates upon cooling the solution at room temperature. On the other hand, this crystalline form is characterized by the following infrared, DSC and X-ray spectra:

IR ($cm^{-1}$): 3058; 2966; 2633; 1588; 1464; 1436; 1347; 1275; 1207; 1161; 1086; 1049; 1027; 85; 950; 898; 850; 805; 772; 709.

DSC: onset temperature: 134.5° C.; peak temperature: 146.0° C.

X-ray spectrum (2θ): 6.9; 9.2; 9.3; 13.3; 14.8; 15.0; 17.6; 17.8; 19.2; 19.6; 20.8; 21.9; 23.2; 24.2; 24.6; 25.0.

These two crystalline forms are a further object of the invention and can be conveniently used for the preparation of pharmaceutical forms, in particular those intended for the therapy of Parkinson's disease. Said pharmaceutical forms may be prepared with conventional techniques and excipients, according to what described, for example, in Remington's Pharmaceutical Sciences Handbook, XXI Ed. Mack Pub., N.Y., U.S.A.

The invention will be now illustrated in greater detail in the experimental section.

DISCLOSURE OF THE FIGURES

FIG. 1: IR spectrum of Rotigotine hydrochloride Form A

FIG. 2: DSC of Rotigotine hydrochloride Form A

FIG. 3: X-ray spectrum of Rotigotine hydrochloride Form A

FIG. 4: IR spectrum of Rotigotine hydrochloride Form B

FIG. 5: DSC of Rotigotine hydrochloride Form B

FIG. 6: X-ray spectrum of Rotigotine hydrochloride Form B

EXPERIMENTAL SECTION

Example 1

Preparation of 2-N-propyl-5-hydroxy tetraline hydrobromide (5)

2-N-Propyl-5-methoxy tetraline base 2 (15 g) was reacted with 100 mL of 48% HBr under reflux for 5 hours with stirring under nitrogen atmosphere. After completion of the reaction, the mixture was cooled to 0° C. and, after one night, the precipitate, consisting of 2-N-propyl-5-hydroxy tetraline hydrobromide 5, was collected by filtration, after which it was washed on the filter with cold water to neutrality. After drying, 19 g of product was obtained, corresponding to a 91% yield. Analysis with chiral HPLC of the enantiomeric composition of the amines recovered from the first precipitate and, respectively, from the solid obtained by evaporating mother liquors to dryness, proved that, starting from an amine 2 with ee 0.94, a crystal of 5 is obtained with ee higher than 0.98. On the other hand, the amine recovered from mother liquors has ee 0.86.

Example 2

Preparation of Rotigotine hydrochloride (1) (Form A)

Step 1—Preparation of Rotigotine

2-N-Propyl-5-hydroxy tetraline hydrobromide (5, 19 g) was finely ground and suspended in 100 mL of water in the presence of 200 mL of dichloromethane. An excess of $K_2CO_3$ (200 mL, 20% aqueous solution) was added under stirring, at a temperature of 5-10° C. The organic phase was separated and extraction was repeated twice, after that the organic phase was washed with aqueous saturated NaCl, dried over sodium sulfate, and evaporated to give an oily residue.

In another round-bottom flask, 56 g of 2-thienylacetic acid was dissolved in 125 mL of toluene. The solution was added with 4.8 g of sodium borohydride in small portions, so that temperature did not exceed 20-25° C. One hour after the end of the addition, 13.6 g of the free amine obtained from hydrobromide 5 was added. The resulting toluene solution was heated at 80-90° C. and kept under nitrogen in these conditions for about 8 hours. After completion of the reaction, the mixture was cooled and carefully added with ethanol to decompose the reaction complex, then poured in ice-water containing 10% sodium carbonate. The organic phase was separated, further extracted with 10% sodium carbonate solution, washed with NaCl saturated solution and evaporated to a residue under reduced pressure.

The basic aqueous phase, containing 2-thienylacetic acid, was carefully acidified with 10% sulfuric acid at 0° C. and extracted three times with ethyl acetate. Evaporation of the organic extract allowed to recover about 40 g of 2-thienylacetic acid.

The toluene phase containing Rotigotine 1 was extracted three times with 200 mL of 3N HCl. Subsequently, the acidic solution was added with $NaHCO_3$ (5% aqueous) to pH 8, and then extracted three times with 200 mL of ethyl acetate. Evaporation of the organic extract and drying provided Rotigotine 1 (80%) as a colourless oil.

Step 2—Preparation of Rotigotine hydrochloride

The oil obtained at step 1 was then dissolved in 100 mL of ethanol; the solution was added with 1.5 equivalents of 37% HCl (5.3 mL), then the solution was evaporated to dryness under reduced pressure.

Step 3—Preparation of Rotigotine hydrochloride Form A

The solid resulting from step 2 was taken up in ethanol (160 mL) and heated under reflux, then added with ethyl acetate (160 mL) and the solution was left to spontaneously cool at room temperature, until incipient crystallization. Filtration provided 10.5 g of Rotigotine hydrochloride Form A (70%).

Example 3

Preparation of Rotigotine hydrochloride (1) (Form B)

Rotigotine hydrochloride Form A (10.5 g), prepared according to the process described in the above example, was dissolved in 100 mL of ethanol at the reflux temperature. The solution was cooled to about 60° C., then added with hexane (100 mL) and the resulting solution was left to cool at room temperature, until incipient crystallization; the resulting solid was filtered with suction, washed with hexane and dried at about 85° C. under vacuum, to give 9.9 g of Rotigotine hydrochloride Form B (94%).

The invention claimed is:

1. A process for the preparation of Rotigotine 1

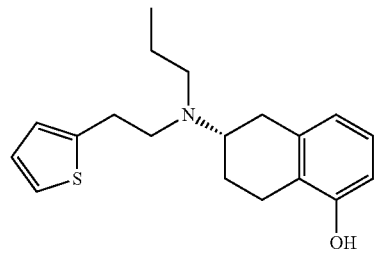

or of a pharmaceutically acceptable salt thereof
which comprises the following steps:
a) demethylating 2-N-propyl-5-methoxy tetraline base 2

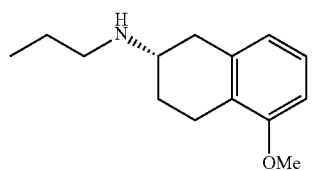

in boiling 48% HBr, to give 2-N-propyl-5-hydroxy tetraline hydrobromide 5 with enantiomeric purity equal to or higher than 98%

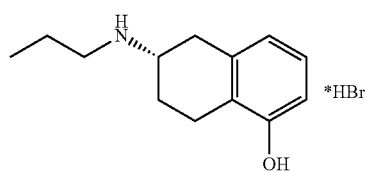

b) liberating 2-N-propyl-5-hydroxy tetraline base 6; and

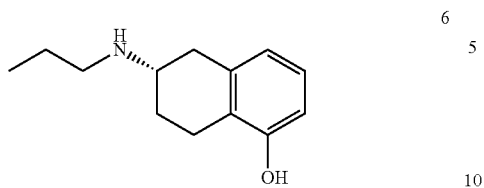

c) reacting by reductive amination amine 6 and 2-thienylacetic acid-sodium borohydride complex in toluene, at a temperature between 80 and 90° C., to obtain Rotigotine 1.

2. The process according to claim 1, further comprising salificating 1 Rotigotine with a pharmaceutically acceptable acid.

3. The process according to claim 2 wherein the pharmaceutically acceptable acid is hydrochloric acid.

* * * * *